United States Patent [19]
Dreitzler et al.

[11] 3,931,730
[45] Jan. 13, 1976

[54] RAMP CURRENT APPARATUS AND METHOD OF SENSITIVITY TESTING

[75] Inventors: David R. Dreitzler, Huntsville; Charles R. Moore, Hazel Green, both of Ala.

[73] Assignee: The United States of America as represented by the Secretary of the Army, Washington, D.C.

[22] Filed: Dec. 23, 1974

[21] Appl. No.: 535,324

[52] U.S. Cl. .................................. 73/35; 73/35 X
[51] Int. Cl.² .......................................... G01N 33/22
[58] Field of Search ............................... 73/35, 167

[56] References Cited
UNITED STATES PATENTS 2,869,364  1/1959  Kabik et al. .................... 73/35 X
2,976,485  3/1961  Bartz ............................. 73/35 X Primary Examiner—James J. Gill
Attorney, Agent, or Firm—Nathan Edelberg; Robert P. Gibson; Jack W. Voigt

[57] ABSTRACT

A ramp current method of sensitivity testing allows a dynamic record to be obtained of the current, voltage, and energy, as well as resistance and instantaneous power necessary to fire electroexplosive devices. This method is most valuable in that useful information is gained from each firing and thus only minimum sampling is utilized. The ramp method also allows a defective item to be detected rather than recorded as a less sensitive device and therefore as an erroneous data point, contributing to more accurate firing data.

6 Claims, 2 Drawing Figures

RAMP CURRENT APPARATUS AND METHOD OF SENSITIVITY TESTING

BACKGROUND OF THE INVENTION

Presently used methods of determining the stimulus necessary to activate a go, no-go device such as an electroexplosive device requires the destructive testing of a large number of the devices. Previously used techniques for evaluating the sensitivity of electroexplosive devices (EED) have incorporated a form of the well established Bruceton test by applying a known fixed value of voltage, current, or energy in the form of a step function to the EED and observing the results (go or no-go testing). This type of sensitivity testing is characterized in that the item will respond or will not respond to the stimulus (go, no-go). In effect the output is a binary or step function of the input as opposed to a proportional relationship. The test is destructive. If the device does function, it is mechanically destroyed by the explosive output. If the EED does not function, its characteristics are altered, which eliminates application of a higher stimulus level to that device as meaningful data in determining its response level.

The probability of response of an EED increases with the level of the stimulus. The functioning characteristics of an EED are determined by sensitivity testing. The type of electrical stimulus used is dependent upon the parameters of interest and the intended application of the device. The most common types of stimuli are constant voltage, constant current, and capacitive discharge. Constant voltage stimulus is typified by a lead acid car battery. An ideal power source of this type is capable of supplying infinite current with no source voltage drop. A constant current source provides a fixed current at whatever voltage the electrical load requires. It can be approximated by a voltage source having an extremely large series resistance compared to the load resistance. In many EED applications a capacitor is used to function a particular EED. The purpose of this type stimuli is to apply a known, predetermined amount of energy to the device. The energy may be calculated by the equation $E = \frac{1}{2}CV^2$, where V is the voltage that the capacitor is charged to and C is the value of capacitance.

The desired sensitivity test is selected on the basis of the particular parameters of interest (voltage, current, energy) and the stimulus is then determined. The objective of the test is to determine the device characteristics with respect to the particular parameter. A sample lot of the device which is representative of the entire device population is then obtained and tested. From these results a prediction is obtained as to how a device selected at random from the entire population should respond.

The most commonly accepted technique for sensitivity testing presently incorporates the well known Bruceton method, which is discussed in the "Ordnance Engineering Design Handbook," ORDP 20-11, page 10–22. Given a sample lot, this technique consists of increasing the stimulus level, in predetermined increments, to the point where the particular EED fires. The stimulus is then decreased by an increment, usually the amount of previously advanced increment if it is known, and another EED is tested. If this device does not function, the stimulus level is again increased by the fixed increment and applied to yet another item. This process is repeated with successive EED's having only one level of stimulus applied thereto until a unit or device fires. The stimulus level is then sequentially decreased with respective EED's until a unit does not fire. The Bruceton method also contains a procedure for obtaining the mean firing current or stimulus and its deviation. The analysis is based on the assumption that deviation of the firing current distribution is a normal or Gaussian type. If it is not the case, the data must be made Gaussian by the introduction of a normalizing factor. In testing EED sensitivity, the data is made to appear Gaussian by using the logarithm of the stimulus. This testing method has the advantage of concentrating the testing about the fifty percent probability firing point. It is noted that these sensitivity testing methods will not reveal the presence of a defective sample, such as a unit with a missing bridgewire. They merely indicate that an EED did not fire, leading to the possibly erroneous presumption that only a higher level of stimulus was required to fire the device.

SUMMARY OF THE INVENTION

A ramp current method of sensitivity testing utilizes a ramp input signal to an electroexplosive device to provide an accurate determination of when the device fires and the potential at which it fires. This provides an accurate means of determining the mean firing range for EED's picked at random for sampling. Since a ramp current is utilized which can provide an ultimate stimulus substantially higher than the firing stimulus range, it readily distinguishes between those EED's which merely have a slightly higher firing point from those which are defective and will not fire. Thus, the data respecting the sensitivity of electroexplosive devices is upgraded, appropriately allowing defective EED's to be recorded as such and not grouped categorically as less sensitive devices.

DESCRIPTION OF THE PREFERRED EMBODIMENT

Figure 1:
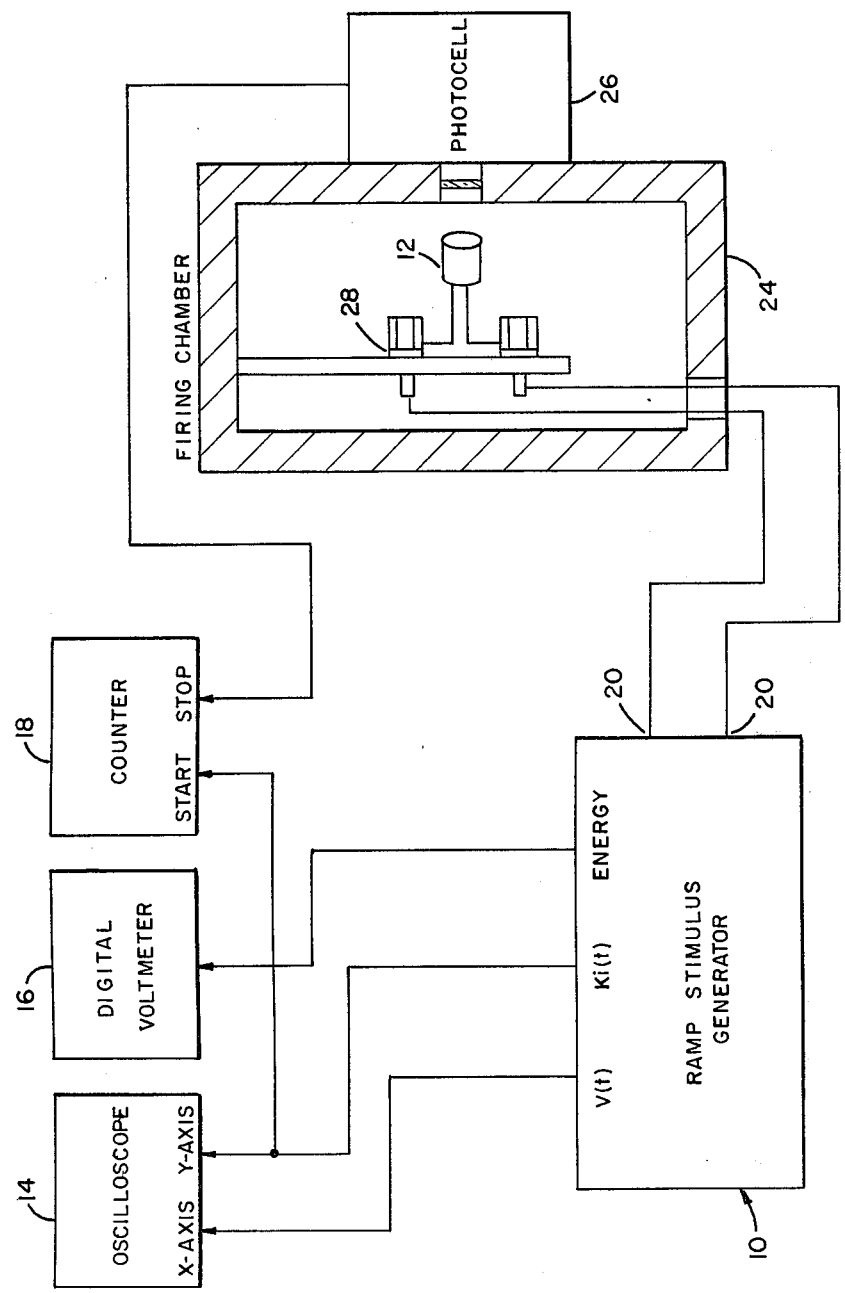
FIG. 1 is a simplified diagrammatic view of a preferred embodiment of the ramp current testing circuit with extraneous circuit components omitted.

The ramp current method of sensitivity testing for electroexplosive devices utilizes a preferred method in that accomplished by the circuit embodiment of FIG. 1. A ramp stimulus generating circuit 10 provides the stimulus to electroexplosive device 12, and activates suitable recording instruments — oscilloscope 14, voltmeter 16, and counter 18. The particular electronic circuitry contained in the ramp stimulus generator produces a current that increases linearly with time. This current is applied from the ramp stimulus output terminals 20 to the EED 12 being destructively tested. The EED is enclosed in a suitable protective firing chamber 24, which also provides environmental conditioning. A light sensor 26 detects the flash produced when EED 12 fires and produces an output pulse to a "stop" input of counter 18. Associated with the linearly increasing output current, the ramp stimulus generating circuitry also produces electrical signals proportional to the related output voltage $v(t)$, output current function $Ki(t)$, and output energy applied to the EED. These proportional time varying parameters are applied to the respective recording devices 14, 16, and 18. Outputs v(t) and Ki(t) are coupled to cathode ray oscilloscope 14 to obtain an x-y plot of the current as a function of voltage. The digital voltmeter 16 is coupled to the energy output of generator 10, for providing a voltage reading proportional to energy used by the electroexplosive device. The counter 18 is coupled to the function of current Ki(t) for recording the functioning or operating time of the EED. The EED 12 within chamber 24 is connected to binding posts 28 whereby the electrical signal stimulus from generator 10 is coupled thereto.

Figure 2:
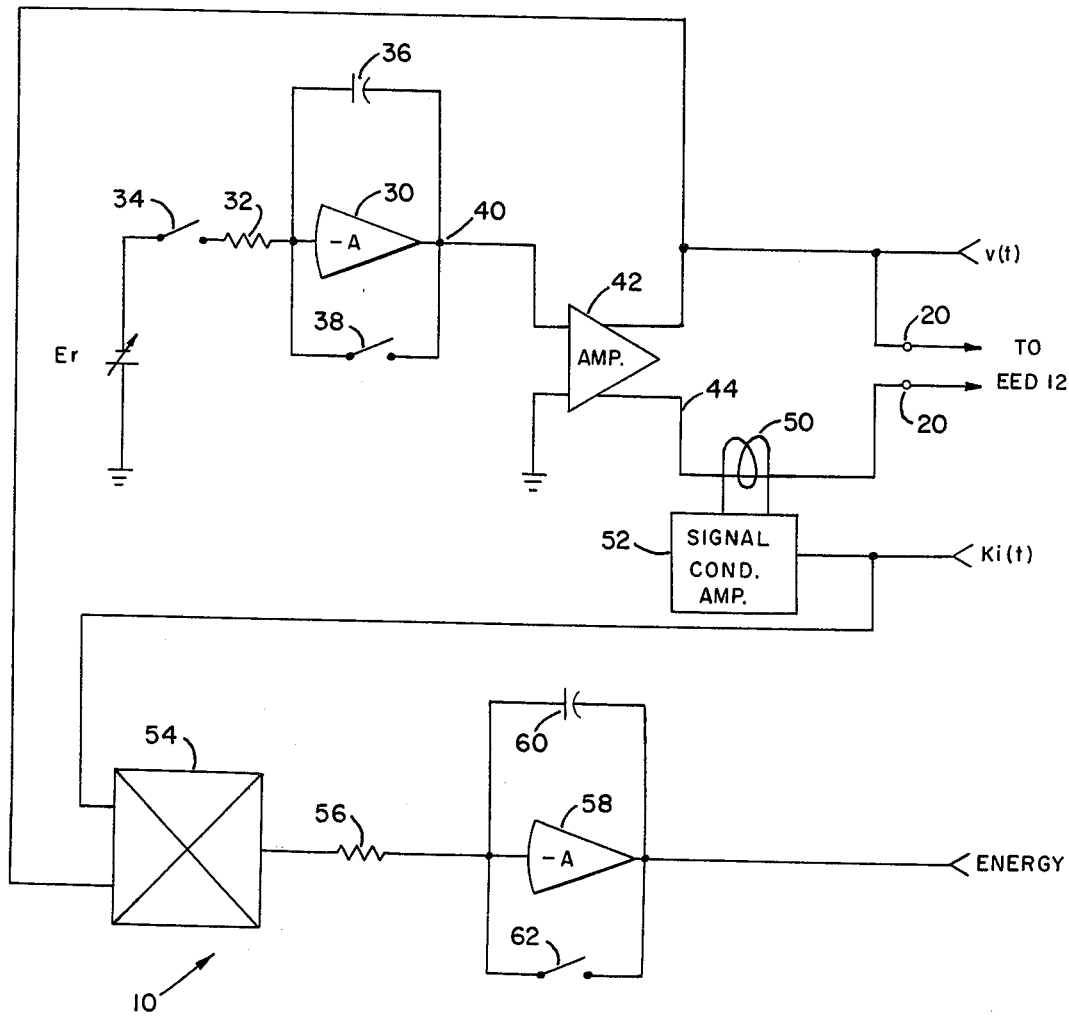
FIG. 2 is a schematic block diagram of the ramp stimulus generator of FIG. 1.

A schematic diagram of the ramp stimulus generating circuitry 10 is as shown in FIG. 2. A voltage source $E_r$ supplies an adjustable potential to an operational amplifier 30 through a series resistor 32 and a series switch 34. A feedback capacitor 36 is strapped across amplifier 30 in parallel with a normally open reset switch 38. A linearly increasing voltage ramp is produced by the operational amplifier 30 in conjunction with the input resistor 32 and the feedback capacitor 36 forming an analog integrator. The adjustable constant reference voltage $E_r$ is applied to the input of the operational integrator upon closing switch 34. The output of the integrator is thus a linearly increasing ramp with time. Varying $E_r$ makes it possible to change the slope of the ramp by changing the magnitude of $E_r$ for any given test. Switch 38 is provided to reset the integrator before the start of each test. The integrator output 40 is applied to the input of a power amplifier 42. The output of the power amplifier 42 is linearly increasing current coupled to output terminals 20 to provide sufficient current to initiate the EED 12. This output is also sampled and used to provide the output voltage as a function of time, v(t).

A current probe 50 is coupled around an related output lead 44 from amplifier 42 to terminal 20 and is used to sense the higher frequency current function which flows through EED 12 without altering the stimulus waveform. The output of probe 50 is coupled to signal conditioning amplifier 52. The current probe output signal from amplifier 52 is a voltage Ki(t) which is directly proportional to the current being measured. For very low frequencies of operation, a current sampling resistance of low resistance in the output line 44 could replace probe 50 and provide the same function. These parameters, V(t) and Ki(t), are then applied to the input of an analog multiplier 54. An output from multiplier 54 is applied to the input of an analog integrator consisting of an input resistor 56 and an operational amplifier 58 in parallel with feedback capacitor 60. A reset switch 62 allows reset of this system after each operation. The integrator output is thus proportional to the energy applied to the EED as a function of time. These time varying parameters, v(t), Ki(t), and energy, are then applied to the recording devices 14, 16, and 18.

In operation, switch 34 of the ramp generator 10 is closed, applying $E_r$ to amplifier 30. This results in the increasing ramp current being coupled across EED 12 and the simultaneously coupling of the ramp voltage v(t), current function Ki(t), and energy to the recording circuitry.

Counter 18 starts timing when the signal Ki(t) is coupled thereto. When EED 12 fires the flash from the exploding bridgewire is sensed by photocell 26 and counter 18 is stopped by an output signal from the photocell, indicating the lapsed time from start or application of the stimulus to firing of the EED. Since the EED bridgewire is broken during firing, no more current flows through the EED, and signals applied to the voltmeter are terminated, leaving a digital record of the firing voltage. Switches 38 and 62 are then momentarily closed to reset amplifiers 30 and 58 and terminate the voltage applied to the oscilloscope. Switch 34 is opened to remove $E_r$ from amplifier 30. Obviously these switches can be operated separately or ganged such that switches 38 and 62 are opened when switch 34 is closed and are closed when switch 34 is opened.

If the EED is defective and fails to fire within the normally acceptable time, the ramp current continues to increase. A predetermined limit or maximum time for current application is established, for example −30 seconds. If the EED does not fire after this time, the test is terminated. No flash would occur to stop the counter; however, in terminating the tests, switches 34, 38, and 62 are operated which interrupts the input energy applied to the load and to the recording devices. The maximum voltage and current coupled to the recording devices indicate the magnitude required to function the device or, if the device does not fire, the ultimate magnitude of the signals coupled thereto. Typically, for an established "no-fire" condition, the energy supplied to the EED may increase by an order of 10 or more over the nominal firing energy, indicating a defective device.

A working model of the circuit for providing the ramp stimulus testing can be constructed utilizing operational amplifiers as well as the following components or equivalents thereto:

| | |
|---|---|
| Oscilloscope 14 | Tektronic Model 549 Storage Oscilloscope |
| Voltmeter 16 | Hewlett-Packard Model 3450B |
| Counter 18 | Hewlett-Packard Model 5300A |
| Amplifier 42 | Hewlett-Packard Model 6824A |
| Current Probe 50 | Hewlett-Packard Model 456A |
| Amplifier 52 | Bell & Howell Model 8-115 |
| Multiplier 54 | Analog Device Company Model 429. |

The ramp current stimulus apparatus for sensitivity testing may be used wherever there is a need to evaluate the ignition parameters and characteristics of any electroexplosive device. In the ramp stimulus method of EED testing, each device tested will function at some point along the input ramp voltage if it is not defective. Thus, meaningful data concerning the firing current, voltage, or energy of a squib or other EED can be obtained from only one firing with the ramp stimulus method.

The voltage, current, resistance, and energy is observed as a function of time which is particularly useful in analyzing new electro-explosive devices. The instantaneous power delivered to the device and the total energy delivered from the time of initial application of the given stimulus is also available as a function of time. This information alone can be used to calculate the firing parameters for other forms of stimulus. Thus, it is possible to infer the device response to a unit step function stimulus from the unit ramp response since the unit step is the time integral of the unit ramp.

This method allows the sensitivity of the device to the rate of energy application to be readily evaluated. This information is useful in obtaining the thermal properties of the device and lends itself equally as well with a voltage source or a current source as the ramp stimulus, the energy being readily available in either case.

Obviously many modifications and variations of the present invention are possible. It is to be understood therefore that within the scope of the appended claims the invention may be practiced otherwise than as specifically described.

We claim:

1. Apparatus for sensitivity testing electroexplosive devices, comprising: a ramp stimulus generator for providing a variable ramp current output for coupling to said electroexplosive device; an oscilloscope coupled to said ramp stimulus generator and responsive to the voltage and current coupled to said electroexplosive device to provide an x–y plot thereof; a counter coupled to said ramp stimulus generator for activation when current is applied to said electroexplosive device and for indicating the time in which current is supplied to said electroexplosive device; and a light sensor adjacent said electroexplosive device having an output coupled to said counter for stopping said counter when said electroexplosive fires.

2. Apparatus as set forth in claim 1 wherein said ramp stimulus generator comprises a variable voltage source; an output power amplifier; an integrating operational amplifier coupled between said voltage source and said power amplifier for providing a linear ramp voltage to said power amplifier, the output of said power amplifier being coupled across said electroexplosive device and being further coupled to provide output voltage to said oscilloscope; a signal conditioning amplifier for providing a current function output signal to said oscilloscope and said counter, said signal being proportional to current through said electroexplosive device; and current sensing means coupled to the output of said power amplifier for sensing current flow through said electroexplosive device, said current sensing means being connected as an input to said signal conditioning amplifier.

3. Apparatus as set forth in claim 2 wherein said ramp stimulus generator further comprises an analog multiplier having an output and first and second inputs; said inputs being coupled respectively to said power amplifier output voltage and to said signal conditioning amplifier output function of current; and an integrating operational amplifier having an input coupled to the output of said multiplier and an output for providing an output signal proportional to the energy expended in said electroexplosive device.

4. Apparatus as set forth in claim 3 and further comprising a voltmeter coupled to said energy output for providing a voltage reading proportional to energy expended in said electroexplosive device.

5. A method of sensitivity testing individual electroexplosive devices, comprising the steps of:
applying an increasing ramp current stimulus to the device;
monitoring the time from which current is initially applied to the device until it is interrupted;
plotting an oscilloscope trace of the voltage versus a function of the current applied to the device; and
recording a digital record of the increasing voltage applied to the device until it is interrupted by firing of the device or termination of the input ramp current stimulus.

6. A method of sensitivity testing individual electroexplosive devices as set forth in claim 5 wherein said recording of a digital record further comprises the steps of:
sampling the ramp voltage coupled to said device;
sampling a function of the current coupled through said device;
processing the sampled ramp voltage and current function through an analog multiplier and integrating operational amplifier to obtain the energy coupled to the device; and
recording the energy stimulus to obtain said digital record of voltage applied to the device.

* * * * *